(12) United States Patent
Lee

(10) Patent No.: US 10,596,314 B2
(45) Date of Patent: Mar. 24, 2020

(54) INFUSION FLOW REGULATOR

(71) Applicant: Hanvit MD Co., Ltd, Daejeon (KR)

(72) Inventor: Doo Yong Lee, Daejeon (KR)

(73) Assignee: Hanvit MD Co., Ltd, Daejeon (KR)

( * ) Notice: Subject to any disclaimer, the term of this patent is extended or adjusted under 35 U.S.C. 154(b) by 154 days.

(21) Appl. No.: 15/519,638

(22) PCT Filed: Sep. 24, 2015

(86) PCT No.: PCT/KR2015/010054
§ 371 (c)(1),
(2) Date: Apr. 17, 2017

(87) PCT Pub. No.: WO2016/064098
PCT Pub. Date: Apr. 28, 2016

(65) Prior Publication Data
US 2017/0239416 A1 Aug. 24, 2017

(30) Foreign Application Priority Data

Oct. 20, 2014 (KR) ........................ 10-2014-0141917

(51) Int. Cl.
*A61M 5/168* (2006.01)
*A61M 5/36* (2006.01)
*A61J 1/20* (2006.01)

(52) U.S. Cl.
CPC ............ *A61M 5/16804* (2013.01); *A61J 1/20* (2013.01); *A61M 5/168* (2013.01); *A61M 5/36* (2013.01);

(Continued)

(58) Field of Classification Search
CPC .... A61M 2205/3379; A61M 2205/583; A61M 2207/00; A61M 5/16804; A61M 5/36
See application file for complete search history.

(56) References Cited

U.S. PATENT DOCUMENTS 7,028,927 B2 * 4/2006 Mermet ............ A61M 5/16881
137/556
8,029,480 B2 * 10/2011 Lee .................... A61M 5/16881
251/149.5

(Continued)

FOREIGN PATENT DOCUMENTS

EP       1 312 388 B1   12/2004
JP      2004-275739 A   10/2004

(Continued)

OTHER PUBLICATIONS

International Search Report for PCT/KR2015/010054 filed on Sep. 24, 2015.

*Primary Examiner* — Quynh-Nhu H. Vu

(57) ABSTRACT

The present invention relates to an infusion flow adjuster which is used in order to adjust the flow rate of an infusion solution to be administered when performing infusion therapy, and relates to an infusion flow adjuster in which an arc-shaped flow path for adjusting the distance through which the infusion solution passes and a circular flow path for inducing discharge of the infusion solution that has passed through the arc-shaped flow path are constituted in a single plane, and which is easy to produce as a product for accurately adjusting the flow rate, affords convenience of handling being provided with a handle in a suitable position, and also, in addition to allowing fine adjustment of the flow rate, limits the maximum flow rate to an appropriate value, so being convenient to use during actual infusion therapy.

7 Claims, 11 Drawing Sheets

(52) U.S. Cl.
CPC ............... *A61M 2205/3379* (2013.01); *A61M 2205/583* (2013.01); *A61M 2207/00* (2013.01)

(56) References Cited

U.S. PATENT DOCUMENTS

| | | |
|---|---|---|
| 2004/0140444 A1 | 7/2004 | Beck et al. |
| 2005/0065480 A1 | 3/2005 | Lee et al. |
| 2007/0293828 A1 | 12/2007 | Lee |
| 2012/0215181 A1 | 8/2012 | Lee |
| 2013/0178805 A1* | 7/2013 | Baid ................. A61M 5/16877 604/246 |

FOREIGN PATENT DOCUMENTS

| | | |
|---|---|---|
| KR | 10-2003-0044181 A | 6/2003 |
| KR | 10-0468222 B1 | 1/2005 |
| KR | 10-1058539 B1 | 8/2011 |

* cited by examiner (a)

(b)

INFUSION FLOW REGULATOR

CROSS REFERENCE PARAGRAPH

This application is a U.S. National Stage of PCT/KR2015/010054, filed Sep. 24, 2015, which claims the priority benefit of Korean Patent Application No. 10-2014-0141917, filed on Oct. 20, 2014 in the Korean Intellectual Property Office, the disclosures of which are incorporated herein by reference.

TECHNICAL FIELD

The present invention relates to an infusion flow regulator used in regulating a flow rate of an infusion solution to be administered when an infusion solution treatment is performed, and more particularly, to an infusion flow regulator that can be easily manufactured as a product capable of precisely regulating a flow rate because an arc-shaped flow path configured to regulate a distance through which an infusion solution passes and a circular flow path configured to guide discharge of the infusion solution that has passed through the arc-shaped flow path are formed on a single plane, can be easily handled because of a handle formed at an appropriate position, and is convenient to use during an actual infusion solution treatment because of its abilities to finely regulate a flow rate and limit the maximum flow rate to an appropriate value.

BACKGROUND ART

As illustrated in a use state view of FIG. 1, an infusion solution set (10) is a medical appliance for regulating a flow rate of an infusion solution in an infusion solution bottle (1) to a target flow rate according to a prescription and administering the infusion solution to a patient, and includes a drop chamber (11) connected to the infusion solution bottle (1) and having an inner space in which the infusion solution falls in the form of drops (11a) (unit: gtt) to be collected in a lower portion thereof, a tube (12) connected to the drop chamber (11) and configured to enable the infusion solution collected in the lower portion of the drop chamber (11) to flow to an injection needle (14), an infusion flow regulator (13) mounted at a middle of the tube (12) to regulate a flow rate of the infusion solution, and the injection needle (14) installed at an end of the tube (12).

Here, the infusion flow regulator (13) illustrated in FIG. 1 is an IV flow regulator capable of more precisely regulating a flow rate of an infusion solution compared to a roller clamp in which a flow rate of an infusion solution is regulated by changing a cross-sectional area of a flow path of the tube (12) by vertical movement of a roller. When a rotation angle of a first body (13c) rotatably coupled to a body (13a) is adjusted according to gradations (13b), a length of an inner flow path is changed, and a flow rate can be regulated.

As disclosed in Korean Patent Publication No. 10-2003-0044181 and Korean Patent No. 10-0468222, the infusion flow regulator (13) includes an arc-shaped flow path in which a length passed through by an infusion solution varies depending on rotation of the first body (13c) and a discharge guide groove configured to guide the infusion solution that has passed through the arc-shaped flow path to be discharged. Also, the infusion flow regulator (13) has a structure in which the arc-shaped flow path and the discharge guide groove are respectively formed as an arc and a circular groove and are covered with rubber packing to be sealed.

However, in Korean Patent Publication No. 10-2003-0044181 and Korean Patent Registration No. 10-0468222, because the arc-shaped flow path and the discharge guide groove are formed at different installation surfaces, the arc-shaped flow path and the discharge guide groove are each sealed with separate rubber packing, and a structure thereof is complex. Therefore, although the arc-shaped flow path and the discharge guide groove should be able to accurately regulate a flow rate by rotation of the first body by the two installation surfaces, the rubber packing installation structure, and the coupling structure between the body and the first body being precise manufactured and then assembled, precisely manufacturing is difficult due to the complexity of the structure, and a flow rate may be inaccurately regulated due to a manufacturing error in an actually assembled state.

Meanwhile, to handle the infusion flow regulator (13) exemplified in FIGS. 1 and 2A-2B, the body (13a) should be held with one hand, and the first body (13c) should be rotated with the other hand. However, here, the body 13a should be stably held so that the tube (12) does not move. For this, although it is preferable that portions held by both hands face each other and a held portion of the body (13a) be aligned with the tube (12), this is not so according to FIGS. 1 and 2A-2B.

PRIOR ART DOCUMENT

[Patent Document]
(Patent document 1) KR 10-2003-0044181 A 2003. 06.09
(Patent document 2) KR 10-0468222 B 2005. 01.17

DISCLOSURE

Technical Problem

The present invention has been devised to solve problems such as difficulty, inaccuracy, and inconvenience of use of the prior art described above, and is directed to providing an infusion flow regulator which has a structure that enables the infusion flow regulator to be manufactured as a product capable of accurately regulating a flow rate, can be easily manufactured because of a simple structure, and can regulate a flow rate while stably gripping a tube so that the tube does not move.

Technical Solution

To achieve the above objective, an infusion flow regulator capable of regulating a flow rate by varying a flow path between an inlet port 110 and an outlet port 120 according to the present invention includes a first body 200 having, on a single flat surface, a circular flow path 230 formed as a recessed groove along a circle, an arc-shaped flow path 210 formed as a recessed groove along an arc having a relatively larger radius than that of the circular flow path 230, and a connecting flow path 220 formed as a recessed groove to connect one end of the arc-shaped flow path 210 to the circular flow path 230; a sealing member 300 formed of a single plate to cover the surface of the first body 200 on which the circular flow path 230, the arc-shaped flow path 210, and the connecting flow path 220 are formed, and having a circular flow path outlet 320 formed as a through-hole at one point on the circular flow path 230 to be in communication with the circular flow path 230 and an arc-shaped flow path inlet 310 formed as a through-hole at one point on the arc-shaped flow path 210 to be in communication with the arc-shaped flow path 210; and a second body 100 having the inlet port 110 connected to the arc-shaped flow path inlet 310, and the outlet port 120 connected to the circular flow path outlet 320, wherein the first body 200 is rotatably mounted in the second body 100 while the sealing member 300 is interposed between the first body 200 and the second body 100 and fixed so as not to rotate.

In the second body 100, the inlet port 110 and the outlet port 120 may be disposed to face each other with respect to a rotating axis, and a handle 130 formed long from the rotating axis to each of the inlet port 110 and the outlet port 120 and configured to be gripped by a hand may be disposed at a rear surface opposite to a surface on which the first body 200 is mounted.

A concavo-convex portion and gradations may be formed at an outer circumferential surface of the first body 200 in a circumferential direction, and the gradations may be formed to be closer to the second body 100 than the concavo-convex portion.

A cross-sectional area of the connecting flow path 220 may be formed to be relatively larger than that of the circular flow path 230.

A width of the arc-shaped flow path 210 may be uniform over an entire section, and a depth thereof may gradually deepen from the other end, which is blocked, to the one end connected to the connecting flow path 220 such that a cross-sectional area thereof may be gradually increased toward the one end. A width and a depth of the circular flow path 230 may be uniform over an entire section such that a cross-sectional area thereof may also be uniform, a diameter of the arc-shaped flow path inlet 310 may be the same as the width of the arc-shaped flow path 210, and a diameter of the circular flow path outlet 320 may be the same as the width of the circular flow path 230.

A cross-sectional area of the circular flow path 230 may be the same as a maximum cross-sectional area of the arc-shaped flow path 210, and flow rates with respect to a water level difference of 1 m may be engraved in the first body 200 as gradations.

A cross-sectional area of the circular flow path 230 may be formed to be relatively larger than the maximum cross-sectional area of the arc-shaped flow path 210.

From the other end, which is blocked, to the one end connected to the connecting flow path 220, a cross-sectional area of the arc-shaped flow path 210 may be formed to be gradually increased and then be decreased. The decreasing section may be relatively shorter than the increasing section, and a decreasing amount may be small at an initial stage in which the decreasing section is reached from the increasing section and then be gradually increased.

Effects of the Invention

In the present invention configured as above, manufacturing is easy because an arc-shaped flow path and a circular flow path are formed on a single flat surface and a sealing member is formed as a single plate, and precise processing is possible without an error because a surface for forming the arc-shaped flow path and the circular flow path is a single flat surface, thereby ensuring flow rate regulating accuracy of an assembly.

Also, in the present invention, the first body can be rotated while the handle is naturally gripped vertically and the tube is stabilized so as not to move because a first body is mounted at one surface of both surfaces of a second body and a handle in the form of connecting a connection portion of the tube is disposed at the other surface, and the first body can be stably rotated because of being held with both hands facing each other, thereby solving a problem in that an error may occur due to movement of the tube when a flow rate is regulated and after the flow rate is regulated.

Further, with respect to arrangement positions of a protrusion and gradations which are disposed in a circumferential direction at an outer circumferential surface of the first body, the gradations are not hidden from sight while the protrusion is gripped by the protrusion being formed at an edge side of the first body and the gradations being formed to be closer to the second body than the protrusion, and readability is high because a size of each of the gradations can be relatively larger compared to when the gradations are engraved in a front surface of the first body.

Further, in the present invention, because a cross-sectional area of a connecting flow path configured to connect between an arc-shaped flow path and a circular arc path is formed to be larger than that of the circular flow path, an infusion solution introduced into the circular flow path can be guided to smoothly flow along two routes formed in the circular flow path, and bubbles remaining in the circular flow path can be easily removed completely.

Further, in forming the arc-shaped flow path of the present invention, a section in which a flow rate will be precisely regulated is secured as a long section by gradually increasing from a blocked portion, and a maximum flow rate is appropriately limited by limiting an arc-shaped flow path inlet and a circular flow path outlet or making a cross-sectional area decreased toward the connecting flow path, which is substantially a section not used in regulating a flow rate, in a section close to the connecting flow path, thereby providing a precise flow rate regulating ability and stability in use.

MODES OF THE INVENTION

Hereinafter, exemplary embodiments of the present invention will be described with reference to the accompanying drawings in order to enable those of ordinary skill in the art to easily embody and practice the invention.

Figure 3:
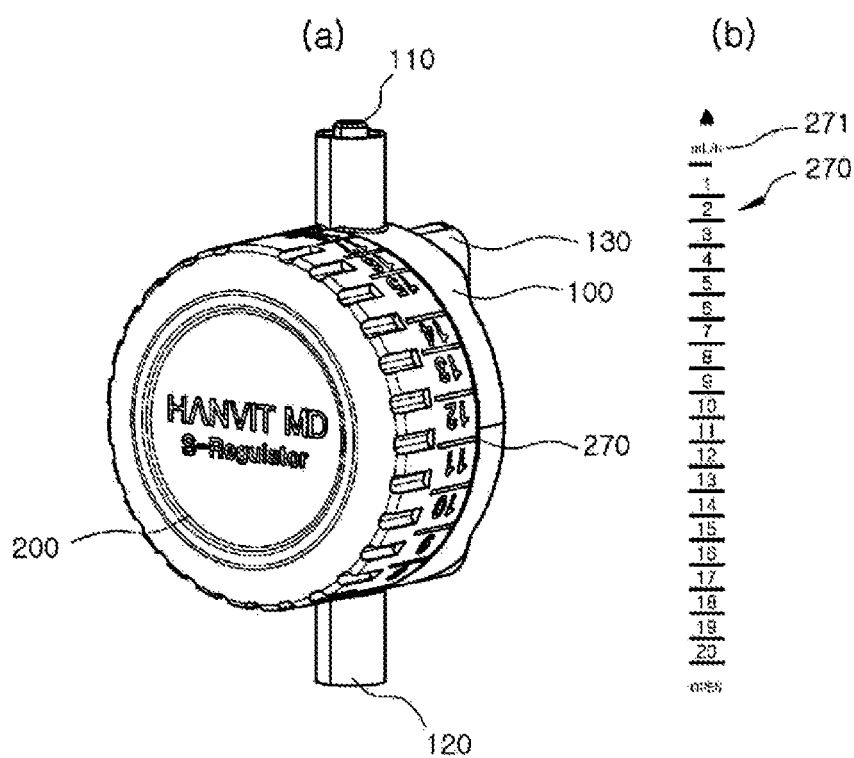
FIGS. 3A and 3B are front perspective views (a) of an infusion flow regulator according to an embodiment of the present invention, and an unfolded view (b) of gradations 270 engraved along a circumferential direction of a first body 200.
Figure 4:
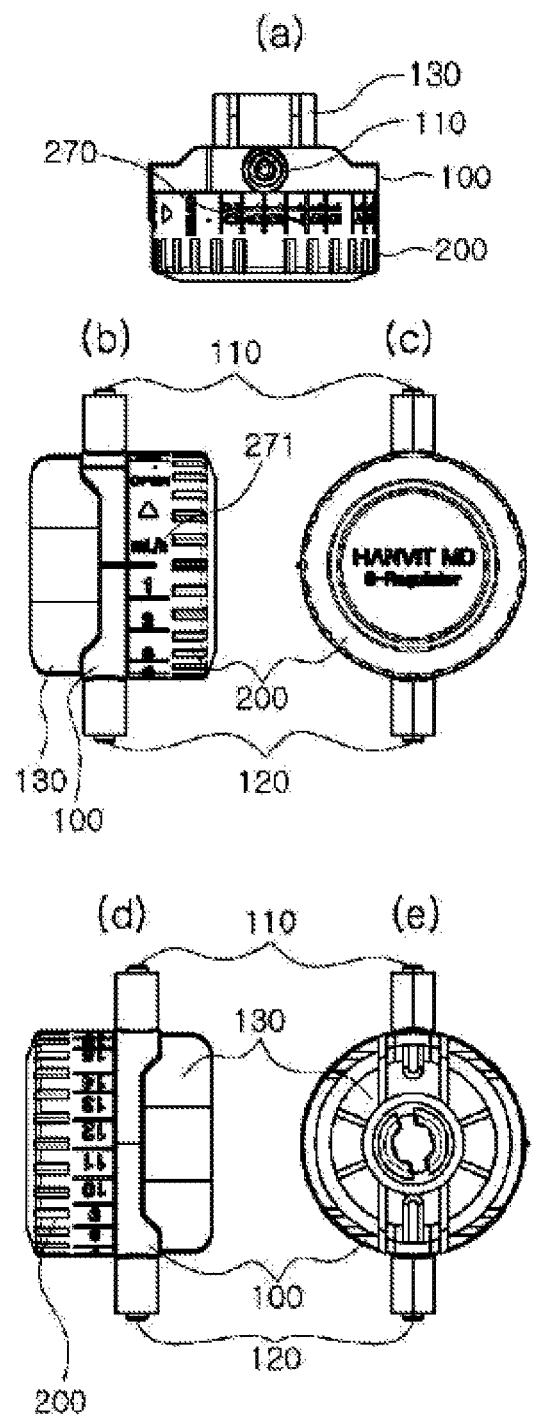
FIGS. 4A-4E are a top view (a), a left view (b), a front view (c), a right view (d) and a rear view (e) of the infusion flow regulator according to the embodiment of the present invention.

FIGS. 3A-3B and 4A-4E are views for describing an exterior of an infusion flow regulator according to an embodiment of the present invention. FIGS. 3A-3B are a front perspective view (a) and an unfolded view (b) of gradations 270 engraved along a circumferential direction of a first body 200, and FIGS. 4A-4E are a top view (a), a left view (b), a front view (c), a right view (d) and a rear view (e).

Figure 5:
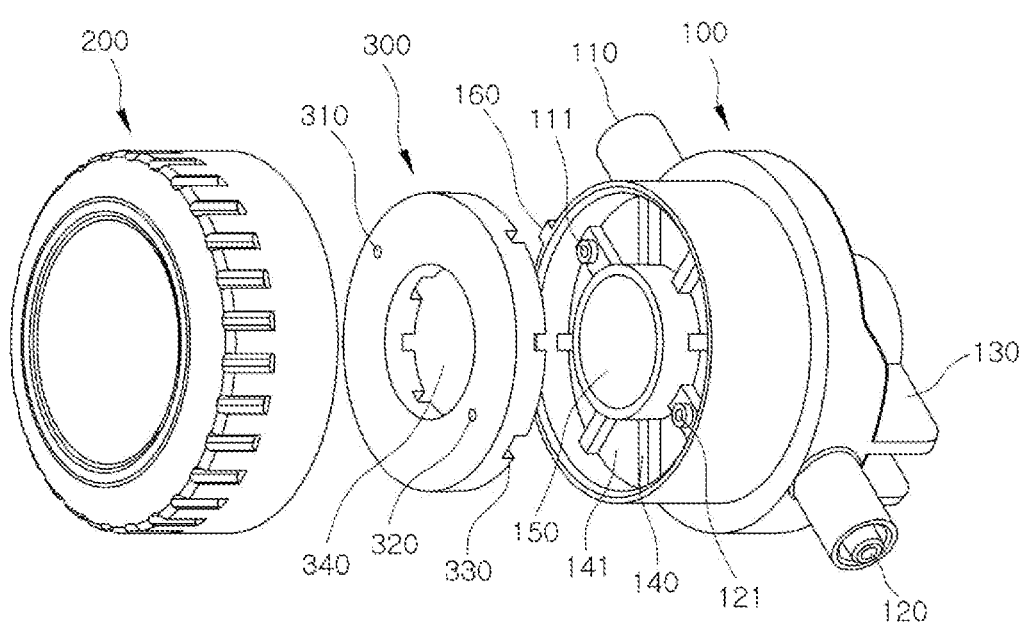
FIG. 5 is a front exploded perspective view of the infusion flow regulator according to the embodiment of the present invention.
Figure 6:
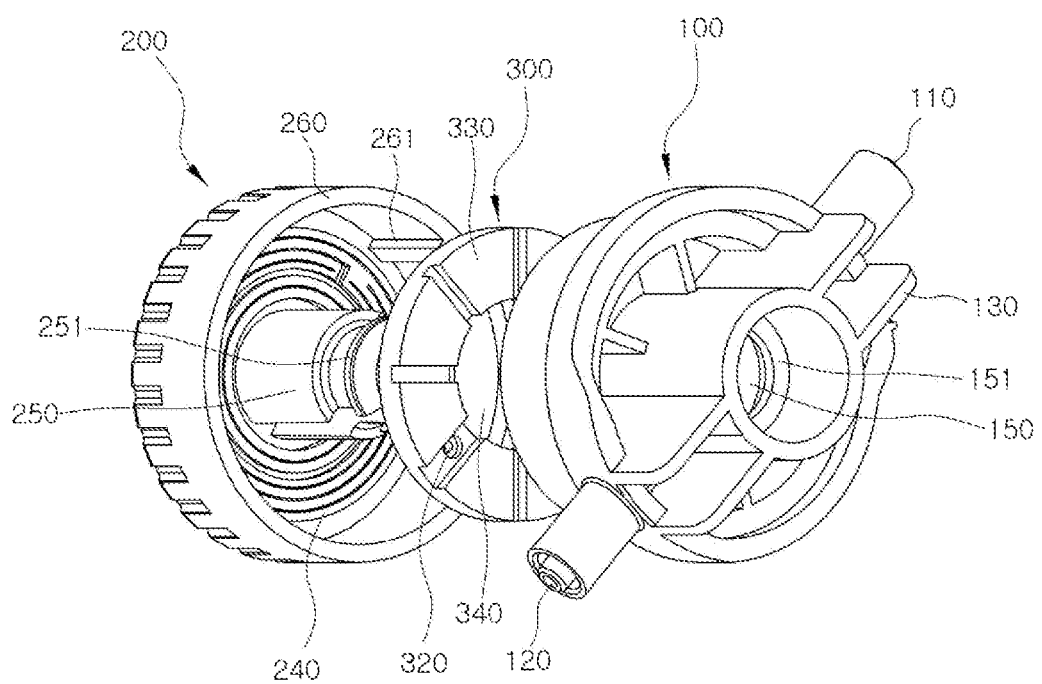
FIG. 6 is a rear exploded perspective view of the infusion flow regulator according to the embodiment of the present invention.
Figure 7:
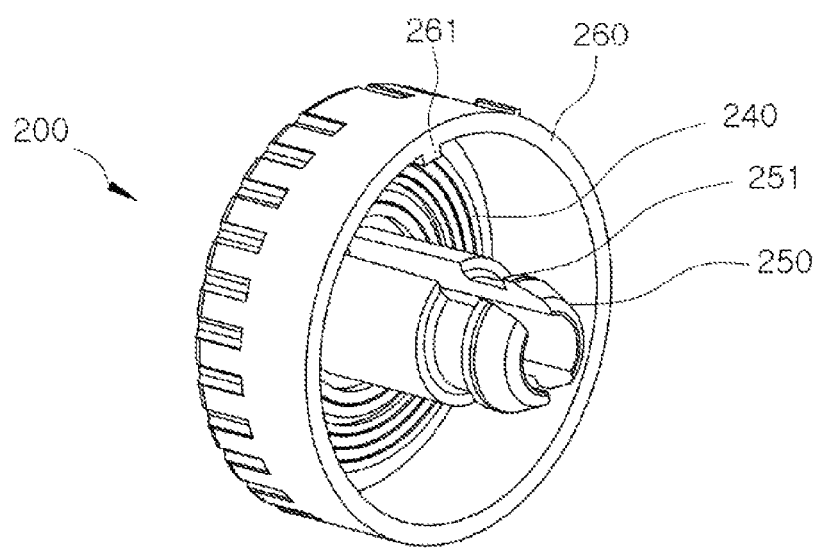
FIG. 7 is a rear perspective view of the first body 200.
Figure 8:
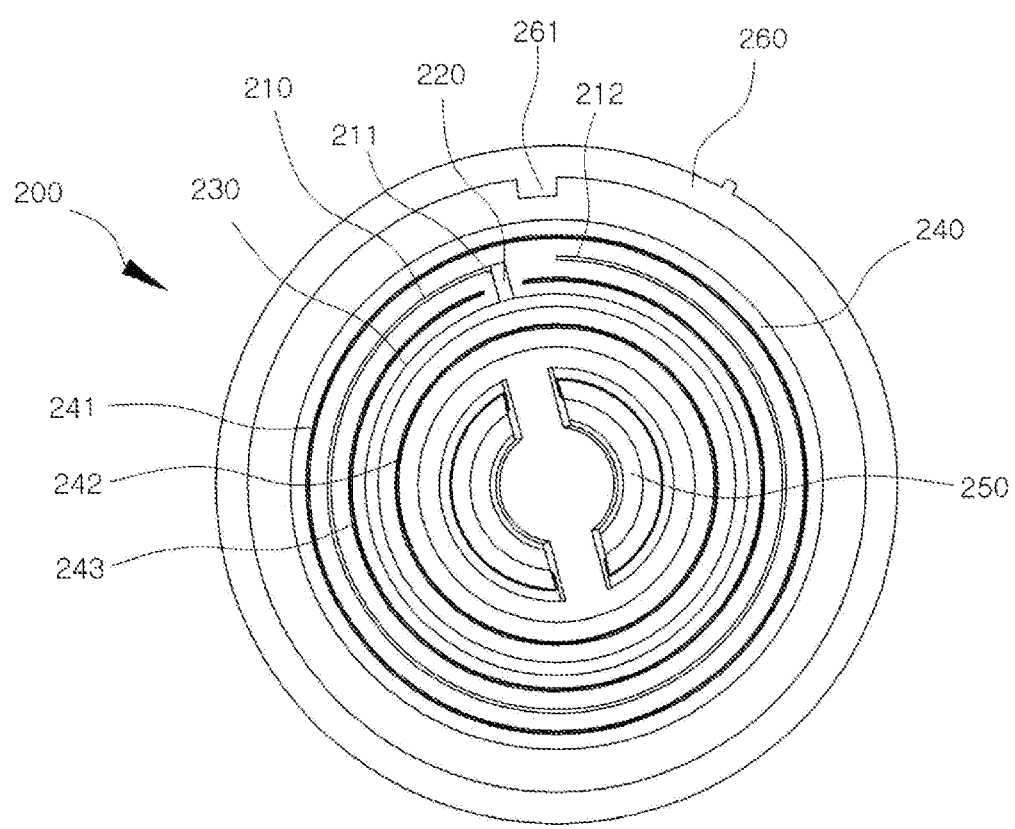
FIG. 8 is a rear view of the first body 200.
Figure 9:
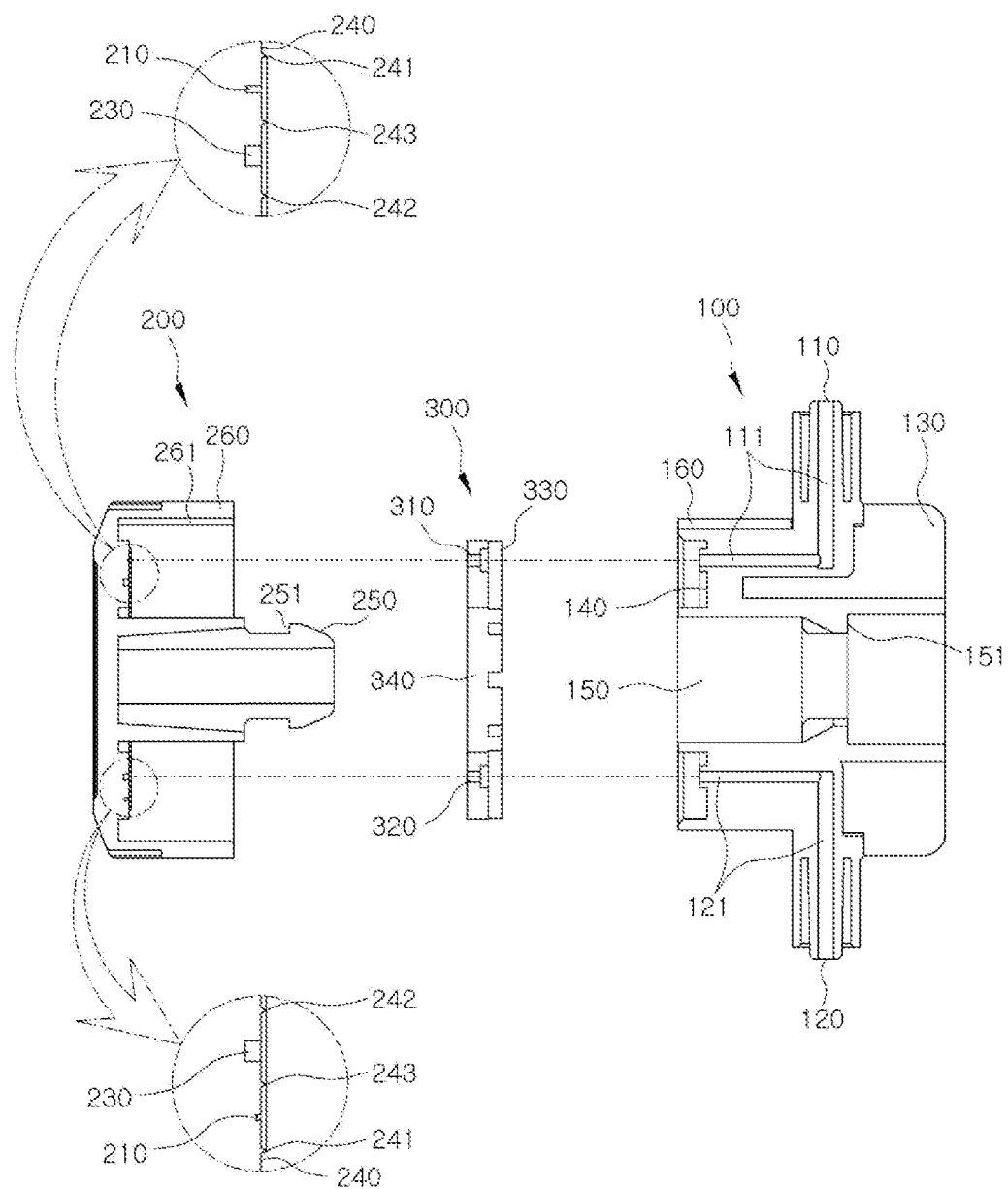
FIG. 9 is an exploded cross-sectional view of the infusion flow regulator according to the embodiment of the present invention.
Figure 10:
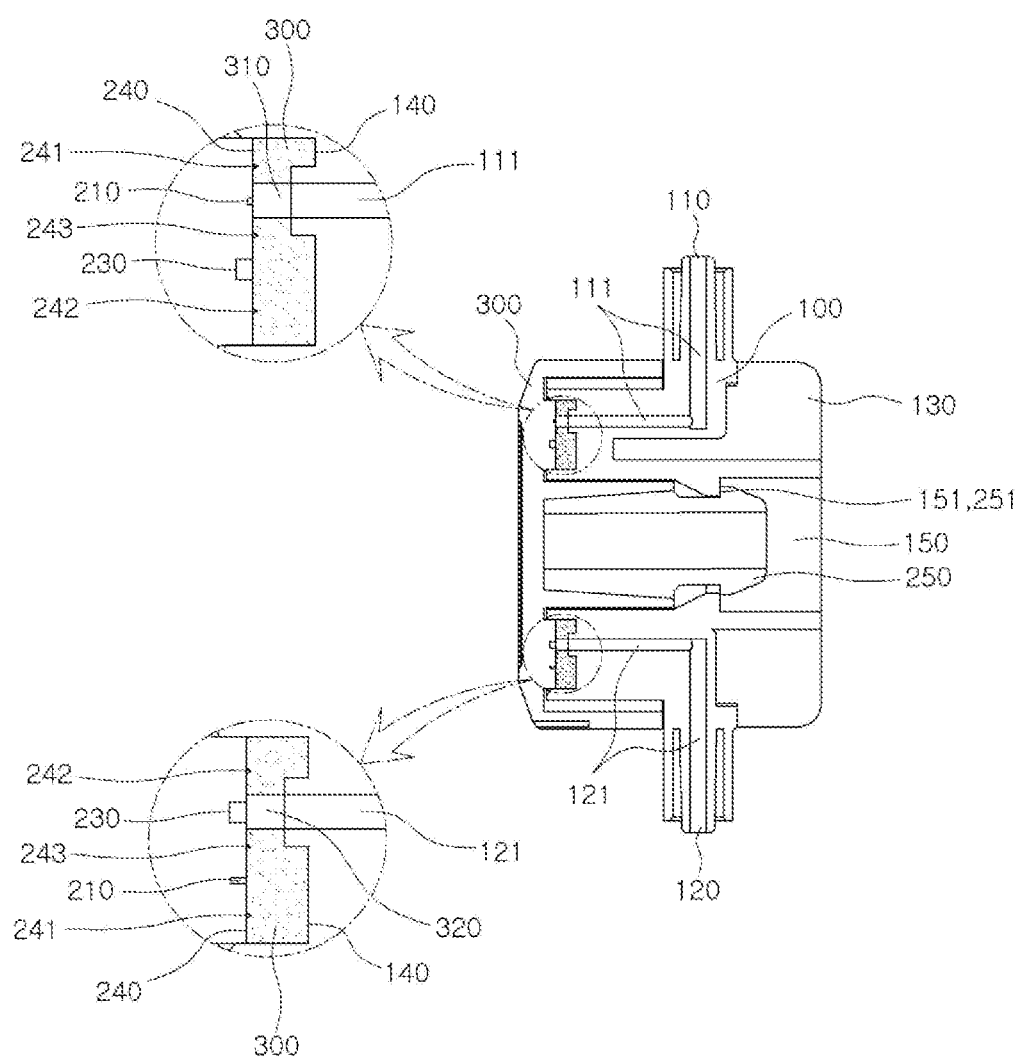
FIG. 10 is an assembled cross-sectional view of the infusion flow regulator according to the embodiment of the present invention.

FIGS. 5 to 10 are views for describing elements of the infusion flow regulator according to the embodiment of the present invention. FIG. 5 is a view illustrating an exploded infusion flow regulator in a front perspective view, FIG. 6 is a view illustrating the exploded infusion flow regulator in a rear perspective view, FIG. 7 is a rear perspective view of the first body 200, FIG. 8 is a rear view of the first body 200 when viewing a flow path forming surface 240, FIG. 9 is an exploded cross-sectional view of the infusion flow regulator, and FIG. 10 is an assembled cross-sectional view of the infusion flow regulator.

Referring to the drawings, an infusion flow regulator according to an embodiment of the present invention includes a second body 100 having an inlet port 110 and an outlet port 120 configured to have both cut tubes of an infusion solution set fastened and connected thereto so that an infusion solution is introduced through the inlet port 110, a flow rate of the infusion solution is regulated by a first body 200, and then the infusion solution is discharged through the outlet port 120, the first body 200 rotatably mounted on the second body 100 and having a flow path arranged between the inlet port 110 and the outlet port 120 to enable a flow rate to be regulated by a flow path configured to change a flow resistance by having a rotation angle changed, and a sealing member 300 interposed between the second body 100 and the first body 200 to seal the flow path of the first body 200.

The second body 100 includes a fastening hole 150 formed to pass through from a front side to a rear side and having a hooking part 151 formed at an inner circumferential surface, the inlet port 110 formed to protrude upward to have the tube inserted and fixed therein to enable the infusion solution to be introduced from an upper portion, the outlet port 120 formed to protrude downward to face the inlet port 110 located thereabove with respect to the fastening hole 150 and have the tube inserted and fixed therein to enable the infusion solution to be discharged downward, a sealing member seating surface 140 formed at a front surface of a forward protruding portion to enable the sealing member 300 to be seated thereon and having a plurality of grooves 141 radially formed around the fastening hole 150, an inflow path 111 formed with a deeply recessed groove in the sealing member seating surface 140 to be in communication with the inlet port 110, a discharge path 121 formed with a deeply recessed groove in the sealing member seating surface 140 to be in communication with the outlet port 120, a stopper 160 formed on an outer circumferential surface of the forward protruding portion to form the sealing member seating surface 140, and a handle 130 formed at a rear surface of the second body 100, formed vertically long toward the inlet port 110 and the outlet port 120 with respect to the fastening hole 150 and connected to each of the inlet port 110 and the outlet port 120, and configured to be gripped by a hand.

Here, because a protrusion 330 of the sealing member 300 which will be described below is inserted into the grooves 141 formed at the sealing member seating surface 140, the sealing member 300 is not rotated but fixed to the second body 100 when seated on the sealing member seating surface 140.

Further, because an entrance of the inflow path 111 and an entrance of the discharge path 121 which are exposed at the sealing member seating surface 140 are respectively in communication with an arc-shaped flow path inlet 310 and a circular flow path outlet 320 of the sealing member 300 which will be described below, the inlet port 110 is connected to the arc-shaped flow path inlet 310 which will be described below through the inflow path 111, and the outlet port 120 is in communication with the circular flow path outlet 320 which will be described below through the discharge path 121.

The handle 130 may be disposed at a rear surface opposite to a front surface to which the first body 200 is coupled. In this way, while the handle 130 is held by one hand and the second body 100 is prevented from moving, the first body 200 may be rotated by the other hand. The handle 130 may be formed of a transparent or semi-transparent material and enable a connection state of the tube and an infusion solution flowing through the inflow path and the discharge path to be visually recognized.

The first body 200 includes an insertion piece 250 formed to protrude from a center of a rear surface and to be inserted into the fastening hole 150 of the second body 100 to serve as a rotating axis, a flow path forming surface 240 formed as a single flat surface near the insertion piece 250 of the rear surface and closely adhered to the sealing member seating surface 140 of the second body 100 while the sealing member 300 is interposed between the first body 200 and the second body 100 when the first body 200 is mounted on the second body 100, an arc-shaped flow path 210, a connecting flow path 220, and a circular flow path 230 formed on the flow path forming surface 240, an outer circumferential surface part 260 formed to surround an outer circumferential surface of a portion made to protrude to form the sealing member seating surface 140 of the second body 100 when mounted on the second body 100 at a predetermined interval, a hooking protrusion 261 formed to protrude from an inner circumferential surface of the outer circumferential surface part 260 to be hooked and stopped by the stopper 160 at a predetermined rotation angle when the first body 200 is rotated, and the gradations 270 which are formed along a circumferential direction of the outer circumferential surface part 260.

According to an embodiment of the present invention, the insertion piece 250 is formed by cutting a hollow tube along a longitudinal direction and dividing the hollow tube into two pieces. When cutting the hollow tube, the hollow pieces are cut with a predetermined width so that an interval is formed between the two pieces. Accordingly, when being inserted into the fastening hole 150 of the second body 100, the insertion piece 250 may be elastically deformed inward and inserted. Also, the insertion piece 250 has a hook 251 which is caught by the hooking part 151 formed at the inner circumferential surface of the fastening hole 150 when inserted into the fastening hole 150 of the second body 100 so that the insertion piece 250 is not detached from the fastening hole 150. Also, because the insertion piece 150 may be rotated while inserted into the fastening hole 150 of the second body 100 and prevented from being detached therefrom, only the first body 200 may be rotated while the second body 100 is gripped.

The circular flow path 230 is formed to be a recessed groove and formed so as to be a circular shape around the insertion piece 250, thereby forming a circular closed curve.

The arc-shaped flow path 210 is also formed to be a recessed groove and formed so as to be an arc shape having a radius larger than that of the circular flow path 230 around the rotating axis. Thus, a closed curve is not formed. Here, a central angle of the arc-shaped flow path 210 formed in the arc shape is preferably formed close to 360° and may be, for example, 330°. Here, forming positions of the hooking protrusion 261 and the stopper 160 of the second body 100 are aligned so that the hooking protrusion 261 and the stopper 160 stop rotation of the first body 200 at a point deviating from the central angle of the arc-shaped flow path 210 (i.e., a point deviating from the arc-shaped flow path 210) after being aligned to the other end 212 of the arc-shaped flow path 210.

In this way, one end 211 of the arc-shaped flow path 210 which is concentric with the circular flow path 230 is connected to the circular flow path 230 by the connecting flow path 220 formed to extend in the shape of a recessed groove toward the circular flow path 230. The other end 212 of the arc-shaped flow path 210 is remains blocked. Accordingly, a flow path which forms an arc from the other end 212 of the arc-shaped flow path 210 and is then connected to the circular flow path 230 by the connecting flow path 220 at the one end 211 is formed.

The arc-shaped flow path 210, the connecting flow path 220, and the circular flow path 230 formed as described above form the flow path which is covered and sealed by the sealing member 300 which will be described below.

According to an embodiment of the present invention, cross-sectional shapes of the arc-shaped flow path 210, the connecting flow path 220, and the circular flow path 230 are different from one other as follows.

The arc-shaped flow path 210 has a uniform width throughout an entire section. However, because a depth thereof gradually deepens from the other end 212, which is blocked, to the one end 211 which is connected to the connecting flow path 220, a cross-sectional area is gradually increased from the other end 212 to the one end 211.

Because the connecting flow path 220 is connected to the one end 211 of the arc-shaped flow path 210, the connecting flow path 220 has the same depth as that of the one end 211 of the arc-shaped flow path 210, and a width thereof is formed so that the cross-sectional area of the connecting flow path 220 is relatively larger than that of the circular flow path 230.

The cross-sectional size of the connecting flow path 220 is additionally described as follows.

Because the circular flow path 230 forms a closed circle, a path through which an infusion solution introduced through the connecting flow path 220 is discharged through the circular flow path outlet 320 of the sealing member 300 which will be described below includes two routes. However, before administering the infusion solution, a process in which a predetermined amount of infusion solution sequentially passes through the arc-shaped flow path 210 and the circular flow path 230 is then discarded is performed to discharge bubbles in the arc-shaped flow path 210 and the circular flow path 230. Because some of the bubbles in a relatively longer route of the two routes formed in the circular flow path 230 may remain without being discharged, the bubbles may be administered to a patient together with the infusion solution while the infusion solution is being administered to the patent.

Therefore, in the embodiment of the present invention, to completely remove bubbles from the circular flow path 230, the cross-sectional area of the connecting flow path 220 is made to be larger than the cross-sectional area of the circular flow path 230, and the infusion solution that has passed through the connecting flow path 220 is induced to flow by being divided into two routes of the circular flow path 230. Consequently, bubbles in a relatively longer path are also discharged together with the infusion solution.

Because a width and a depth of the circular flow path 230 are uniform throughout an entire section, a cross-sectional area thereof is also uniform throughout the entire section. Here, the depth of the circular flow path 230 is equal to the depth of the connecting flow path 220 and thus also becomes equal to the depth of the one end 211 of the arc-shaped flow path 210. Consequently, the infusion solution smoothly flows when flowing from the one end 211 of the arc-shaped flow path 210 to the circular flow path 230 through the connecting flow path 220.

Because the cross-sectional area of the connecting flow path 220 is larger than the cross-sectional area of the circular flow path 230 as described above, the width of the circular flow path 230 is formed to be smaller than the width of the connecting flow path 220.

When the cross-sectional area of the circular flow path 230 and the cross-sectional area of the arc-shaped flow path 210 are compared, the cross-sectional area of the circular flow path 230 is equal to or relatively larger than the maximum cross-sectional area of the arc-shaped flow path 210. According to an embodiment of the present invention, the maximum cross-sectional area of the arc-shaped flow path 210 becomes a cross-sectional area of the one end 211 connected to the connecting flow path 220.

Consequently, when the cross-sectional area of the circular flow path 230 is equal to the cross-sectional area of the one end 211 which is the maximum cross-sectional area of the arc-shaped flow path 210, it signifies that the depth and the width of the circular flow path 230 are also equal to those of the one end 211.

When the cross-sectional area of the circular flow path 230 is larger than the cross-sectional area of the one end 211 which is the maximum cross-sectional area of the of the arc-shaped flow path 210, it signifies that the depths of the circular flow path 230 and the one end 211 are equal whereas the width of the one end is widened. According to an embodiment of the present invention, a change in the circular flow path 230 may have a substantial influence on flow rate regulation. According to Korean Patent Publication No. 10-2003-0044181 and Korean Patent Registration No. 10-0468222, the path corresponding to the circular flow path 230 of the present invention serves only to receive and discharge the infusion solution passed through the path corresponding to the arc-shaped flow path 210 of the present invention. However, the circular flow path 230 of the present invention may have a relatively much smaller cross-sectional area compared to the prior art. Here, the cross-sectional area of the circular flow path 230 is a value which enables substantially preferable flow rate regulation to be obtained according to experiments or flow analyses.

As described above, in the embodiment of the present invention, because the cross-sectional area of the circular flow path 230 is the same as the maximum cross-sectional area of the arc-shaped flow path 210 or is larger than the maximum cross-sectional area of the arc-shaped flow path 210 within a range in which the circular flow path 230 substantially influences flow rate regulation, a length of a flow path used in flow rate regulation may be formed to be longer than that in Korean Patent Publication No. 10-2003-0044181 and Korean Patent Registration No. 10-0468222 under the same conditions. Accordingly, a product capable of more precisely regulating a flow rate can be manufactured.

Also, by reducing the cross-sectional area of the circular flow path 230, because bubbles are discharged by the infusion solution being immediately filled due to the capillary tube phenomenon or viscosity of the infusion solution, the bubbles are more effectively discharged.

Also, because the gradations 270 are engraved on the basis of Equation 1 below as will be described below, even when the circular flow path 230 is used in regulating a flow rate of the infusion solution, a numerical value indicated by the gradations 270 reflects inherent flow rate characteristics of the infusion flow regulator.

Meanwhile, according to the embodiment of the present invention, as illustrated in FIGS. 8 to 10, annular protrusions 241 and 242 and an arc-shaped protrusion 243 are formed at the flow path forming surface 240 to have a circular or arc shape which is concentric with the arc-shaped flow path 210 or the circular flow path 230.

The annular protrusions 241 and 242 include a protrusion 241 formed to protrude while forming a circle having a diameter larger than that of the arc-shaped flow path 210 to surround an outer side of the arc-shaped flow path 210 and a protrusion 242 formed to protrude while forming a circle having a diameter smaller than that of the circular flow path 230 to have an outer side thereof surrounded by the circular flow path 230. The arc-shaped protrusion 243 is formed to protrude while forming an arc having a diameter smaller than that of the arc-shaped flow path 210 and larger than that of the circular flow path 230, is formed between the arc-shaped flow path 210 and the circular flow path 230, and is cut at a portion at which the connecting flow path 220 is formed, thereby forming an arc shape.

Because the annular protrusions 241 and 242 and the arc-shaped protrusion 243 are formed around the arc-shaped flow path 210 and the circular flow path 230, the sealing member 300 becomes tights when the sealing member 300 is pressed to the flow path forming surface 240. Therefore, when the first body 200 is rotated, the cross-sectional area of each of the arc-shaped flow path 210 and the circular flow path 230 through which an infusion solution passes is not changed.

Further, at an outer edge of the first body 200, a concavo-convex portion is repeatedly formed in a circumferential direction to prevent the slippage of a hand when the first body 200 is gripped by the hand and rotated, and the gradations 270 configured to indicate the rotation angle of first body 200 are also engraved. Here, because the gradations 170 are engraved in an outer circumferential surface of the first body 200 in the circumferential direction, the gradations 270 can be engraved in a size having a larger numerical value compared to when the gradations 270 are engraved in a front surface of the first body 200. In this way, the gradations 270 can be engraved with high readability even when the first body 200 is manufactured in a small size.

Here, because the gradations 270 are disposed closer to the second body 100 than the concavo-convex portion, the gradations 270 are not covered by a hand when the handle 130 of the second body 100 is held by one hand and the concavo-convex portion of the first body 200 is held by the other hand to rotate the first body 200.

The sealing member 300 is formed of, for example, a rubber material to seal the arc-shaped flow path 210 and the circular flow path 230 and is formed as a single plate having a through-hole 340 through which the insertion piece 250 of the first body 200 passes formed at a center to cover the flow path forming surface 240 having the circular flow path 230 and the arc-shaped flow path 210 of the first body 200 formed thereon. Also, when the first body 200 is rotatably mounted on the second body 100, the sealing member 300 is interposed between the second body 100 and the first body 200 and pressed to be closely adhered to the first body 200 to seal the arc-shaped flow path 210 and the circular flow path 230. Here, in the sealing member 300, a plurality of protrusions 330 are formed at a surface opposite to the surface closely adhered to the first body 200, i.e., a surface coming into contact with the second body 100. The protrusions 330 are inserted into the grooves 140 formed at the sealing member seating surface 140 of the second body 100. Therefore, the sealing member 300 is fixed to the second body 100 and does not rotate even when the first body 200 is rotated.

Also, when a state in which the sealing member 300 is closely adhered to the first body 200 is viewed, the sealing member 300 includes the circular flow path outlet 320 formed as a through-hole at one point on the circular flow path 230 to be in communication with the circular flow path 230 and the arc-shaped flow path inlet 310 formed as a through-hole at one point on the arc-shaped flow path 210 to be in communication with the arc-shaped flow path 210.

According to an embodiment of the present invention, a diameter of the arc-shaped flow path inlet 310 is formed to be equal to the width of the arc-shaped flow path 230 in which the width is formed to be uniform throughout the entire section, and a diameter of the circular flow path outlet 320 is formed to be equal to the width of the circular flow path 230 in which the width is formed to be uniform throughout the entire section, thereby enabling the infusion solution to flow smoothly. However, because the inflow path 111 of the second body 100 is connected to the arc-shaped flow path inlet 310, and the discharge path 121 of the second body 100 is connected to the circular flow path outlet 320, the diameter of the inflow path 111 is made to be equal to the diameter of the arc-shaped flow path inlet 310 throughout an entire section or a portion of the inflow path 111 connected to the arc-shaped flow path inlet 310 is made to have a diameter equal to the diameter of the arc-shaped flow path inlet 310, the diameter of the discharge path 121 is made to be equal to the diameter of the circular flow path outlet 320 throughout an entire section or a portion of the discharge path 121 connected to the circular flow path outlet 320 is made to have a diameter equal to the diameter of the circular flow path outlet 320.

When the first body 200 is rotated while the sealing member 300 stays still, a situation in which the circular flow path outlet 320 moves along the circular flow path 230, i.e., a situation in which a point in communication with the circular flow path outlet 320 is changed, occurs, and a situation in which the arc-shaped flow path inlet 310 moves along the arc-shaped flow path 210, i.e., a situation in which a point in communication with the arc-shaped flow path inlet 310 is changed, occurs. Furthermore, even when the first body 200 is rotated within an azimuth range of the arc-shaped flow path 210, the circular flow path outlet 320 is maintained in communication with the circular flow path 230, the arc-shaped flow path inlet 310 is also maintained in communication with the arc-shaped flow path 210, and a distance to the connecting flow path 220 via the arc-shaped flow path 210 is varied, thereby regulating a flow rate by changing a distance which passes through the arc-shaped flow path 210.

When the first body 200 is coupled to the second body 100 while the sealing member 300 configured as above is interposed between the sealing member seating surface 140 and the flow path forming surface 240, the sealing member 300 is pressed, the arc-shaped flow path 210 and the circular flow path 230 are sealed, a flow path connected through the inlet port 110, the inflow path 111, the arc-shaped flow path inlet 310, the arc-shaped flow path 210, the connecting flow path 220, the circular flow path 230, the circular flow path outlet 320, the discharge path 121, and the outlet port 120 is formed.

Also, a point of the arc-shaped flow path 210 in communication with the arc-shaped flow path inlet 310 varies depending on a change in a rotation angle of the first body 200. As a result, a length which passes through the arc-shaped flow path 210 is changed, and a flow rate is regulated. Further, according to an embodiment of the present invention, a change in the lengths of the two routes passing through the circular flow path 230 influences a flow rate and is used in regulating a flow rate.

Next, numerical values engraved at the gradations 270 will be described.

Figure 1:
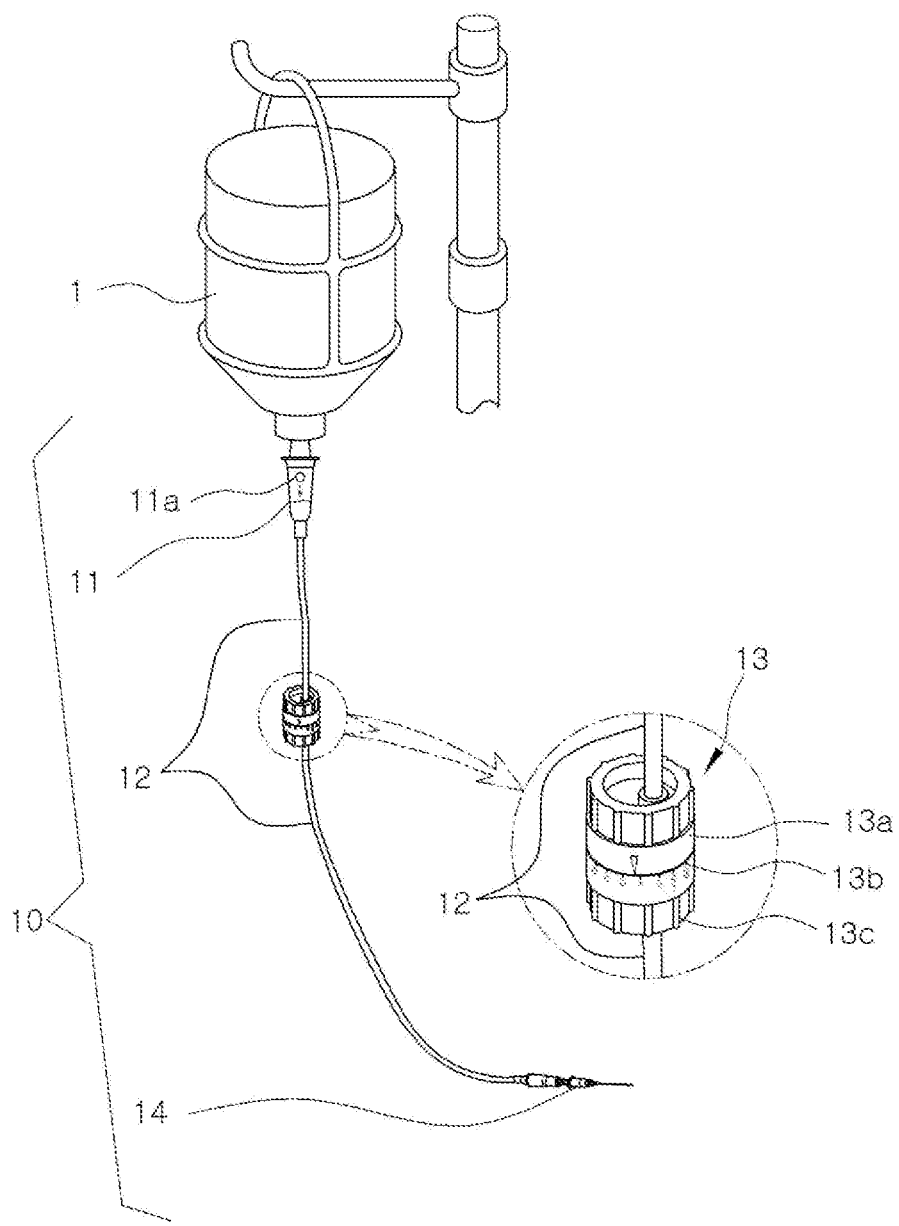
FIG. 1 is a view illustrating a use state of an infusion solution set having a conventional infusion flow regulator mounted therein.
Figure 2:
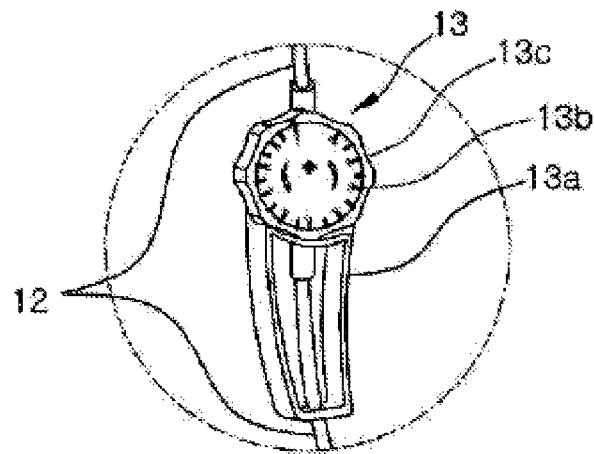
FIGS. 2A and 2B are views illustrating another form of the conventional infusion flow regulator.
Figure 2:
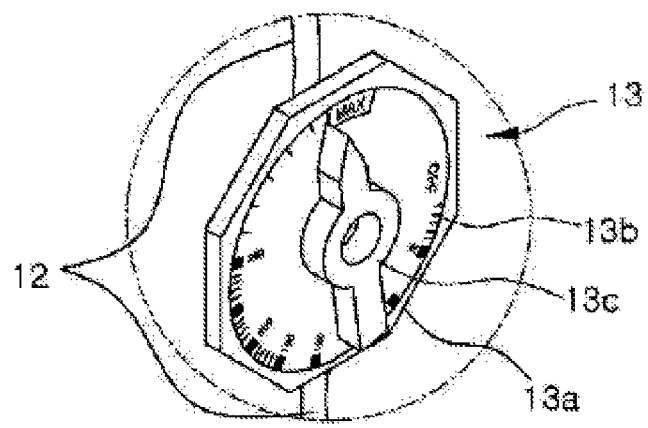

As it can be recognized from the attached FIG. 1 for describing the background art, a flow rate is affected by a height difference between the infusion solution bottle 1 and the injection needle 14 and may be expressed as Equation 1 below according to Korea Patent Registration No. 10-1327862 which has been filed by the applicant of the present invention and registered.

$$Q = C_L \Delta H \qquad \text{[Equation 1]}$$

Here, Q is the flow rate, ΔH is a water level difference according to the height difference between the infusion solution bottle 1 and the injection needle 14, and $C_L$ is a laminar flow overall flow rate coefficient which is defined by an inner flow path of the infusion flow regulator.

According to the embodiment of the present invention, the gradations 270 engraved in the first body 200 are indicated by a value of the laminar flow overall flow rate coefficient $C_L$ which is obtained from Equation 1 when the water level difference is 1 m, and mL/h is marked in the first body 200 as a unit 271. Here, although the unit 271 of the laminar flow overall flow rate coefficient $C_L$ is mL/hm in Equation 1, because mL/h is obtained when the unit m of the water level difference is multiplied, actually engraved numerical values become a flow rate.

According to an embodiment of the present invention, it may be configured so that a change in the circular flow path 230 influences a flow rate. Even in this case, because the value of the laminar flow overall flow rate coefficient $C_L$ which is obtained by the flow rate and the water level difference reflects a change in the circular flow path 230 as well as a change in the arc-shaped flow path 210, the value may be used as a value indicating inherent flow rate characteristics of the infusion flow regulator manufactured according to the present invention.

Figure 11:
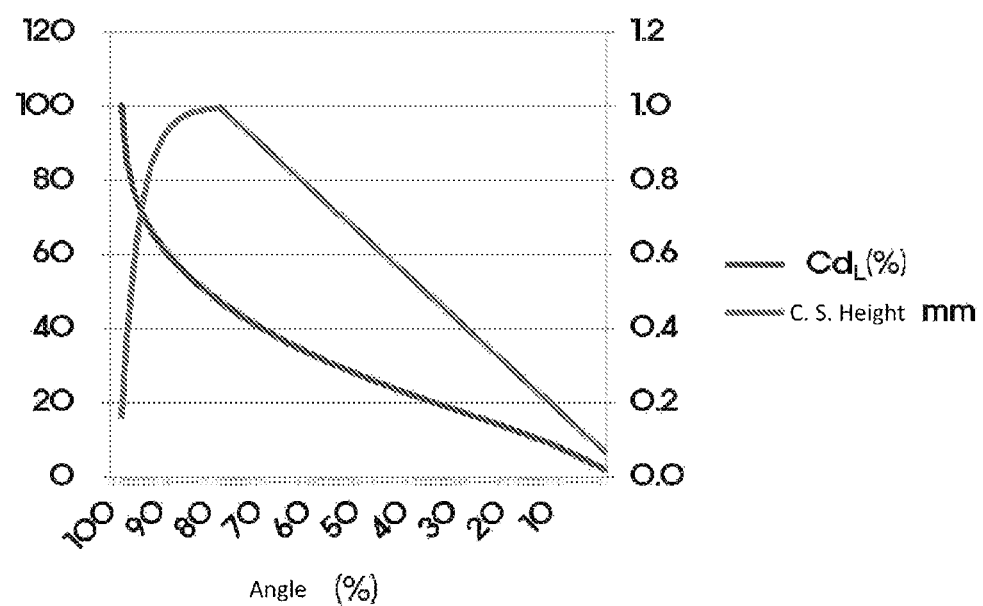
FIG. 11 is a graph illustrating a change in a flow rate according to a change in a depth of an arc-shaped flow path 210 in the infusion flow regulator according to the embodiment of the present invention.

FIG. 11 is a graph for describing another modified embodiment of the arc-shaped flow path 210.

FIG. 11 is a graph illustrating changes in a flow rate according to a rotation angle of the first body of an infusion flow regulator according to another embodiment of the present invention when a width of the arc-shaped flow path 210 is uniformly set as 0.3 mm throughout an entire length and a depth of the arc-shaped flow path 210 is changed along the arc-shaped flow path.

Here, on the X-axis, rotation angles of the first body are indicated as relative angles, and a distance from the other end 212 which is blocked in the arc-shaped flow path 210 to the one end 211 connected to the connecting flow path 220 is indicated as a percentage. That is, relative angles when the one end 211 is assumed as 100 are indicated.

The depth (a blue line in the graph) is gradually increased from the other end 212, which is blocked, to the one end 211 which is connected to the connecting flow path 220, the increasing thereof is stopped at a position near the one end 211, and the depth is gradually decreased from this point. The graph shows relative depths when the maximum depth (a boundary between the increasing section and the decreasing section) is assumed as 100. Therefore, according to an embodiment of the present invention, the cross-sectional area of the arc-shaped flow path 210 gradually increases from the other end 212 to the one end 211 and then decreases. The decreasing section is biased to the one end 211 and is thus formed to be relatively shorter than the increasing section. Here, a decreasing amount is small at an initial stage of the decreasing section but is gradually increased. Therefore, a decreasing amount per unit length is gradually increased toward the one end 211.

As the depth of the arc-shaped flow path 210 is changed as above, the flow rate is shown with a red line in the graph.

According to Equation 1, because the flow rate is proportional to the laminar flow overall flow rate coefficient when the water level difference is constant, the flow rate is indicated as a relative value of the laminar flow overall flow rate coefficient in the graph of FIG. 11.

That is, the laminar flow overall flow rate coefficient which is indicated as a maximum value when the length which passes through the arc-shaped flow path 210 is minimum is indicated by 100, and the remaining section is indicated by a percentage.

According to the graph, when the present invention is actually used for an infusion solution treatment, because a flow rate is changed to be closed to linear in a low flow rate range which is used as a range in which a flow rate is regulated according to a prescription, a flow rate can be easily regulated to be a prescribed flow rate and can be accurately regulated to be the prescribed flow rate.

A section near the one end 211 connected from the arc-shaped flow path 210 to the connecting flow path 220 is not used as a prescribed flow rate range of an infusion solution treatment, but is used in an infusion solution treatment setting process such as discharging air inside the tube and the infusion flow regulator. According to an embodiment of the present invention, because the depth is gradually decreased toward the one end 211 in the section near the one end 211, a flow rate increasing speed is decreased compared to when the depth is gradually increased as in the increasing section of the depth. Accordingly, the maximum value of the flow rate may be limited to an appropriate value to prevent the infusion solution from being excessively discharged in the infusion solution treatment setting process.

In this way, according to an embodiment of the present invention, the infusion flow regulator has advantages in that a flow rate can be precisely regulated by securing a flow rate regulating section to be almost proportional to a rotation angle of the first body 200 and that it is convenient to use because of limiting the maximum flow rate to an appropriate value.

Although a few embodiments of the present invention have been shown and described to exemplify the technical spirit of the present invention, the present invention is not limited to configurations and actions identical to those of the embodiments described above, and various modifications may be made without departing from the scope of the present invention. Therefore, such modifications should be regarded as belonging to the scope of the present invention, and the scope of the present invention should be defined by the claims below.

| [Description of reference numerals] | |
|---|---|
| 100: Second body | |
| 110: Inlet port | 111: Inflow path |
| 120: Outlet port | 121: Discharge path |
| 130: Handle | |
| 140: Sealing member seating surface | 141: Groove |
| 150: Fastening hole | 151: Hooking part |
| 160: Stopper | |
| 200: First body | |
| 210: Arc-shaped flow path | 211: One end  212: The other end |
| 220: Connecting flow path | |
| 230: Circular flow path | |
| 240: Flow path forming surface | 241, 242: Annular protrusions |
| 243: Arc-shaped protrusion | |
| 250: Insertion piece | 251: Hook |
| 260: Outer circumferential surface part | 261: Hooking protrusion |
| 270: Gradations | 271: Unit |
| 300: Sealing member | |
| 310: Arc-shaped flow path inlet | 320: Circular flow path outlet |
| 330: Protrusion  340: Through-hole | |

The invention claimed is:

1. An infusion flow regulator for regulating a flow rate by varying a flow path between an inlet port and an outlet port, the infusion flow regulator comprising:
   a first body having, a circular flow path formed as a first recessed groove along a circle, an arc-shaped flow path having a relatively larger radius than that of the circular flow path and being formed as a second recessed groove, and a connecting flow path formed as a third recessed groove to connect one end of the arc-shaped flow path to the circular flow path, the circular flow path, the arc-shaped flow path, and the connecting flow path being formed on a single flat surface;
   a sealing member formed of a single plate to cover the single flat surface of the first body on which the circular flow path, the arc-shaped flow path, and the connecting flow path are formed, and having a circular flow path outlet formed as a through-hole at one point on the circular flow path to be in communication with the circular flow path and an arc-shaped flow path inlet formed as a through-hole at one point on the arc-shaped flow path to be in communication with the arc-shaped flow path; and
   a second body having the inlet port connected to the arc-shaped flow path inlet, and the outlet port connected to the circular flow path outlet, wherein the first body is rotatably mounted in the second body while the sealing member is interposed between the first body and the second body and fixed so as not to rotate.

2. The infusion flow regulator of claim 1, wherein, in the second body, the inlet port and the outlet port are disposed to face each other with respect to a rotating axis, and a handle formed long from the rotating axis toward each of the inlet port and the outlet port and configured to be gripped by a hand is disposed at a rear surface opposite to a surface on which the first body is mounted.

3. The infusion flow regulator of claim 2, wherein a concavo-convex portion and gradations are formed at an outer circumferential surface of the first body in a circumferential direction, and the gradations are formed to be closer to the second body than the concavo-convex portion.

4. The infusion flow regulator of claim 1, wherein a cross-sectional area of the connecting flow path is formed to be relatively larger than that of the circular flow path.

5. The infusion flow regulator of claim 4, wherein a cross-sectional area of the circular flow path is formed to be relatively larger than a maximum cross-sectional area of the arc-shaped flow path.

6. The infusion flow regulator of claim 1, wherein a cross-sectional area of the circular flow path is formed to be relatively larger than a maximum cross-sectional area of the arc-shaped flow path.

7. The infusion flow regulator of claim 1, wherein, in the second body, the inlet port and the outlet port are disposed to face each other with respect to a rotating axis and aligned in a direction perpendicular to the rotating axis when seen in a cross-sectional view that is obtained by cutting through a center of the infusion flow regulator.

* * * * *